(12) United States Patent
Ulbricht et al.

(10) Patent No.: US 7,476,396 B2
(45) Date of Patent: Jan. 13, 2009

(54) COMPOSITION FOR REMOVING ABNORMAL KERATINOUS MATERIAL

(75) Inventors: Horst Ulbricht, Biebergemünd (DE); Rainer Pooth, Dreieich-Götzenhain (DE); Samuel Shuster, Framlingham (GB)

(73) Assignee: Sanofi-Aventis Deutschland GmbH, Frankfurt Am Main (DE)

( * ) Notice: Subject to any disclaimer, the term of this patent is extended or adjusted under 35 U.S.C. 154(b) by 0 days.

(21) Appl. No.: 10/757,433

(22) Filed: Jan. 15, 2004

(65) Prior Publication Data

US 2004/0146555 A1    Jul. 29, 2004

Related U.S. Application Data

(63) Continuation of application No. 10/156,070, filed on May 29, 2002.

(30) Foreign Application Priority Data

May 30, 2001    (DE)    ................................ 101 26 501

(51) Int. Cl.
*A01N 25/34*    (2006.01)
*A61K 9/00*    (2006.01)
*A61Q 3/00*    (2006.01)

(52) U.S. Cl. ......................... 424/404; 424/400; 424/61

(58) Field of Classification Search ............. 424/78.02, 424/78.03, 401
See application file for complete search history.

(56) References Cited

U.S. PATENT DOCUMENTS

| | | | |
|---|---|---|---|
| 4,402,935 A | 9/1983 | Gordon et al. | |
| 4,721,724 A | 1/1988 | Stettendorf et al. | |
| 4,957,730 A | 9/1990 | Bohn et al. | |
| 5,264,206 A | 11/1993 | Bohn et al. | |
| 5,346,692 A * | 9/1994 | Wohlrab et al. | 424/61 |
| 5,639,740 A * | 6/1997 | Crandall | 514/78 |
| 5,753,256 A | 5/1998 | Cordes et al. | |
| 5,874,074 A * | 2/1999 | Smith | 424/78.02 |
| 5,919,470 A | 7/1999 | Valdez et al. | |
| 5,993,790 A | 11/1999 | Strauss | |
| 6,281,239 B1 * | 8/2001 | Glassman | 514/399 |
| 6,380,236 B2 | 4/2002 | Glassman | |
| 6,429,231 B1 | 8/2002 | Bhagwat et al. | |
| 6,495,602 B1 | 12/2002 | Bhagwat et al. | |
| 6,573,301 B1 | 6/2003 | Glassman et al. | |
| 6,673,842 B2 | 1/2004 | Bhagwat et al. | |
| 6,743,417 B2 | 6/2004 | Glassman et al. | |
| 2002/0197291 A1 | 12/2002 | Ulbricht et al. | |
| 2003/0012749 A1 | 1/2003 | Kraemer et al. | |

FOREIGN PATENT DOCUMENTS

| | | |
|---|---|---|
| DE | 38 10897 A1 | 10/1988 |
| DE | 3720147 | 12/1988 |
| DE | 4212105 | 10/1993 |
| DE | 4337945 | 5/1995 |
| EP | 0 298 271 A1 | 1/1989 |
| GB | 2 202 743 | * 10/1988 |
| GB | 2 202 743 A | 10/1988 |
| WO | WO 8702580 | 5/1987 |
| WO | WO 01/49283 A1 | 7/2001 |

OTHER PUBLICATIONS

Murdan, "Drug delivery to the nail following topical application," in International Journal of Pharmaceutics, vol. 236, Issue 1-2, Apr. 2, 2002, pp. 1-26.*
Bang et al., "Therapeutic Trial of Ointment Base Including Urea and Antifungal Agent as the Treatment of Onychomycosis," Annals of Dermatology, 3:32-36, 1991.
Hay et al., "The Topical Treatment of Onychomycosis Using a New Combined Urea/Imidazole Preparation," Clinical Experimental Dermatology, 13:164-167, 1988.
Patent Abstracts of Japan: JP 59020217 (Published Feb. 1, 1984) to Kawaken Fine Chem Co LTD.
Patent Abstracts of Japan: JP 07291856 (Published Nov. 7, 1995) to Yuutoku Yakuhin Kogyo KK.
Patent Abstracts of Japan: JP 08291057 (Published Nov. 5, 1996) to Yuutoku Yakuhin Kogyo KK.
Patent Abstracts of Japan: JP 09052836 (Published Feb. 25, 1997) to Yanada Makoto Akasaka Rumiko.

* cited by examiner

*Primary Examiner*—Michael G. Hartley
*Assistant Examiner*—Blessing M Fubara
(74) *Attorney, Agent, or Firm*—Finnegan, Henderson, Farabow, Garrett & Dunner, LLP

(57) ABSTRACT

The present invention discloses a pharmaceutical method comprising urea, a hydrophilic film-forming agent, water and/or a water-alcohol mixture that is suitable for the removal of abnormal keratinous material.

11 Claims, No Drawings

COMPOSITION FOR REMOVING ABNORMAL KERATINOUS MATERIAL

This is a continuation of application Ser. No. 10/156,070, filed on May 29, 2002, the contents of which are incorporated by reference herein, which claims the benefit of priority to German patent application no. 10126501.8-41, filed on May 30, 2001.

The present invention relates to a preparation comprising urea, a hydrophilic film-forming agent and water or an alcohol/water mixture. The preparation is useful in the removal of abnormal keratinous material, as is to be observed, for example, in onychomycoses, psoriasis of the nail, or warts. With respect to the abnormal keratinous material, histological hyperparakeratosis is discernible as an abnormally changed layer structure of the skin or of the nail and may be treated with the presently disclosed preparation. Moreover, by means of this invention brittle nails can be rehydrated, thus regenerating, for example, the physiological barrier function of the nails.

Urea has been used in dermatological practice for decades in the form of creams and lotions. Urea changes the structure and the properties of the keratin in the horny layer of the nails. It generally has a hygroscopic action in the horny layer (depending on the carrier), and an antiproliferative action on the epidermis. Urea cleaves disulfide bonds and hydrogen bonds. Through this action, the dead keratinized material is loosened and can then be mechanically detached.

For the detachment or dissolution of changed nails, in particular those that are fungally infested, a cream containing 20% urea (Onychomal®), and an ointment containing 40% urea and the antimycotic Bifonazol® (1%), along have been marketed in a joint pack together with waterproof plasters, an aid for squeezing out, and a nail scraper (Mycospor® nail set). These preparations have been commercially available for over 10 years (Bang D S, Lee Y D, Whang K K, Lee S N, "Therapeutic trial of ointment base including urea and antifungal agent as the treatment of onychomycosis," *Ann. Dermatol.*, 3: 32-6 (1991); Hay R J, Roberts D T, Doherty V R, Richardson M D, Midgley G, "The topical treatment of onychomycosis using a new combined urea/imidazole preparation," *Clin. Exper. Dermatol.*, 13: 164-167, (1988)).

In addition, a nail varnish comprising a hydrophobic film-forming agent, an antimycotic, and urea, which is employed for the treatment of onychomycoses has been described (U.S. Pat. No. 5,346,692).

Disadvantages in the use of these known preparations include frequent maceration and inflammatory changes in the surrounding skin. Moreover, these semisolid preparations necessitate a dressing on the affected sites in order to prevent wiping off and protection of the surrounding tissue, e.g., by covering with zinc paste. Decisive success was denied to the known treatment methods, since such treatments—for example those requiring plasters on the toes and fingers that are bothersome and appear unsightly and must be applied daily—are frequently not completed by the patients for cosmetic reasons and for reasons of time. The time needed for these customary processes is comparatively high, and the acceptance is limited or the compliance is rapidly exhausted, if, for example, more than 3 to 5 nails have to be treated.

For the detachment of indurated areas of skin such as in the case of warts, salicylic acid preparations are customarily used in the form of semisolid preparations such as salicyl petroleum jelly (approximately 20%-60%) or plasters (Guttaplast®). Here too, the disadvantages of the semisolid preparations apply analogously.

The invention provides a preparation comprising a hydrophilic film-forming agent, urea, water and/or an alcohol/water mixture, which overcomes the disadvantages mentioned for the prior art compounds.

The preparation according to the invention is an aqueous or aqueous-alcoholic solution, in which the hydrophilic film-forming agent and urea are dissolved or optionally suspended. A solution is advantageous. After application to the abnormal keratinous material such as warts or fingernails, the preparation rapidly forms an adherent film which is resistant to wiping and rubbing off. The urea penetrates into the abnormal keratin and assists its detachment. Additional covering with plasters, application of a special protective film for the areas of skin surrounding the target site, and daily bathing are not necessary. The preparation according to the invention also prevents undesirable precipitation reactions of the urea that occur locally on the keratinous material being treated. Such precipitation leads to unsightly changes or to possible impairment of the local bioavailability of the urea. The preparation according to the invention makes possible a uniform distribution of the urea on the keratinous material as a result of its composition and its pharmaceutical properties.

Unlike the products known in the prior art, the invention therefore offers several advantages. For instance, the present invention provides markedly improved drug targeting by permitting focused application to the target organ or target site with decreased risk for exposure to the adjacent tissue, and an improved user-friendliness (handling) in the application of the preparation.

The preparation according to the invention therefore provides a formulation comprising
 a) one or more nonvolatile constituents,
 b) urea in an amount from 40 to 70 percent by weight, relative to the nonvolatile constituents of the preparations,
 c) a hydrophilic film-forming agent and
 d) water or an alcohol-water mixture.

The preparation can contain further volatile and nonvolatile constituents as long as the amount of urea, based on the nonvolatile constituents of the preparations, is within the specified range.

The amounts of urea are in each case based on the nonvolatile constituents of the preparation according to the invention and can be from 41 percent by weight to 69 percent by weight, from 45 percent by weight to 65 percent by weight, from 46 percent by weight to 63 percent by weight, or from 55 percent by weight to 63 percent by weight.

Possible hydrophilic film-forming agents include, for example, acrylic/methacrylic acid ester copolymers, polyvinylpyrrolidones, polyvinyl alcohols, vinyl acetate/vinylpyrrolidone copolymers, vinyl acetate/crotonic acid copolymers, methyl vinyl ether/maleic acid copolymers, polyesters, polyester amides, carboxymethylcellulose, hydroxyethylcellulose, hydroxypropylcellulose, hydroxypropylmethylcellulose, and a mixture of two or more of the film-forming agents mentioned. In one embodiment, the hydrophilic film-forming agent is a polyvinylpyrrolidone.

The hydrophilic film-forming agents are employed in amounts from 30 percent by weight to 60 percent by weight, relative to the nonvolatile constituents of the preparation. The amount of the hydrophilic film-forming agents needed will typically depend on the amount of urea in the preparation.

In the aqueous-alcoholic solutions, suitable alcohols include, for example, ($C_1$-$C_6$)-alcohols such as methanol, ethanol, propanol, isopropanol (2-propanol), butanol, pentanol hexanol or mixtures thereof. In one embodiment, ethanol, n-propanol or 2-propanol are employed. In the aqueous-alcoholic solutions, the ratio of alcohol to water typically ranges from 9:1 to 1:9; In one embodiment, the mixture comprises 2 parts of alcohols to 3 parts of water.

Suitable additional excipients include plasticizers, such as glycerol triacetate or 1,2-propylene glycol, and agents for adjusting the pH of the preparations, such as lactic acid or citric acid. In one embodiment, the preparation comprises lactic acid in an amount from 0.5 percent by weight to 5 percent by weight, based on the weight of the entire preparation.

The preparations according to the invention can furthermore contain additives that are customary in cosmetics, such as plasticizers based on phthalate, glyceryl triacetate or camphor, colorants or color pigments, pearl luster agents, sulfonamide resins, sedimentation-delaying agents, silicates, odoriferous substances, wetting agents such as sodium dioctylsulfosuccinate, lanolin derivatives, sunscreen agents such as 2-hydroxy-4-methoxybenzophenone or antibacterially active substances. Colored or pigmented nail varnishes, for example, have the advantage that the preparation according to the invention can be tailored to the perception of beauty of the patient and the nail changes existing in the meantime are not immediately visible to third parties.

The preparation according to the invention is typically prepared by introducing urea and a hydrophilic film-forming agent into water or a water/alcohol mixture and subsequently mixing. In one embodiment, aqueous-alcoholic solutions are prepared in which the urea is present in dissolved form in an amount from 15 percent by weight to 35 percent by weight, based on the weight of the entire solution. The amount of hydrophilic film-forming agent employed is from approximately 15 percent by weight to approximately 35 percent by weight, in each case based on the weight of the entire solution. The amount of the hydrophilic film-forming agent employed generally depends on the amount of urea present in the preparation. The amount of water or aqueous-alcoholic mixture is from 30 percent by weight to 60 percent by weight, or from 35 percent by weight to 55 percent by weight, in each case based on the weight of the entire solution.

The preparation according to the invention is typically applied as a solution to the keratinous materials to be treated. It dries rapidly, forming an adherent film which is resistant to wiping and rubbing off. The solution can be applied, for example, with a brush.

The invention further relates to use of the preparation according to the invention for the detachment of abnormal keratinous material.

The term "abnormal keratinous material" is understood as meaning keratinous material in humans and animals such as warts, calluses, hard skin, or toenails and fingernails that have been changed by fungal attack or psoriatic disease. With respect to the abnormal keratinous material, histological hyperparakeratosis is discernible as an abnormally modified layer structure of the skin or the nail.

The invention also relates to the use of a preparation comprising
  a) one or more nonvolatile constituents
  b) urea in an amount from 30 percent by weight to 90 percent by weight, relative to the nonvolatile constituents of the preparation,
  c) a hydrophilic film-forming agent and
  d) water or an alcohol-water mixture.

The amounts of urea are in each case based on the nonvolatile constituents of the use according to the invention and can be from 35 to 85 percent by weight, from 39 percent by weight to 83 percent by weight, from 46 percent by weight to 63 percent by weight, or from 55 percent by weight to 63 percent by weight.

The hydrophilic film-forming agents are typically employed in amounts from 10 percent by weight to 70 percent by weight, based on the nonvolatile constituents. The amount of the hydrophilic film-forming agents employed depends on the amount of urea. For example, mixtures of approximately 25 percent by weight to 35 percent by weight of urea with 15 percent by weight to 20 percent by weight of hydrophilic film-forming agent may be employed, where the weight percentages are relative to the nonvolatile constituents. Such preparations will generally have a shorter drying time than formulations having a higher or lower content of hydrophilic film-forming agent.

In the uses according to the invention, suitable alcohols, film-forming agents, and additional excipients and nonvolatile constituents are as described above for the the pharmaceutical preparation The amounts of water and/or alcohol, film-forming agents, and additional excipients and non-volatile constituents are also as described above.

The invention also relates to the use of an aqueous solution comprising urea in an amount from 15 percent to 35 percent, or from 25 percent to 33 percent, based on the weight of the entire solution; and a hydrophilic film-forming agent in an amount from approximately 15 percent to approximately 35 percent, or from 17 percent to 25 percent, in each case based on the weight of the entire solution, for the production of a pharmaceutical for the treatment of abnormal keratinous material.

The abnormal keratinous material is detached by applying the preparation, allowing a suitable amount of time for the action of the dried preparation on the keratinous material being treated, and subsequent mechanical removal of the abnormal keratinous material.

The invention further relates to the use of the preparation according to the invention for the hydration of brittle toenails or fingernails.

The present invention is explained in greater detail by means of the following examples, but not restricted to these. If not noted otherwise, the quantitative data are based on the weight.

EXAMPLES

Example 1

A preparation according to the invention has the following composition:

| | |
|---|---|
| Urea | 30% |
| Polyvinylpyrrolidone (molecular weight approximately 11 500) | 20% |
| Demineralized water | 50% |

Example 2

A preparation according to the invention has the following composition:

| | |
|---|---|
| Urea | 30% |
| Polyvinylpyrrolidone (molecular weight approximately 11 500) | 20% |
| Ethanol | 20% |
| Demineralized water | 30% |

Example 3

A preparation according to the invention has the following composition:

| | |
|---|---:|
| Urea | 30% |
| Polyvinylpyrrolidone (molecular weight approximately 11 500) | 20% |
| Propan-2-ol | 20% |
| Lactic acid | 1% |
| Demineralized water | 29% |

Example 4

A preparation according to the invention has the following composition:

| | |
|---|---:|
| Urea | 30% |
| Polyvinylpyrrolidone (molecular weight approximately 11 500) | 20% |
| Lactic acid | 1% |
| Demineralized water | 49% |

Example 5

A preparation according to the invention has the following composition:

| | |
|---|---:|
| Urea | 30% |
| Polyvinylpyrrolidone (molecular weight approximately 15 000) | 20% |
| Propan-2-ol | 20% |
| Demineralized water | 30% |

Example 6

A preparation according to the invention has the following composition:

| | |
|---|---:|
| Urea | 30% |
| Polyvinylpyrrolidone (molecular weight approximately 11 500) | 20% |
| Cremophor EL | 1% |
| Lactic acid | 1% |
| Demineralized water | 48% |

Example 7

Activity Testing

The toenails of two affected patients were treated with the preparation as in Example 3. The preparation of Example 3 was applied once daily to the affected nails with a brush before going to bed. The urea-containing film which formed after the application to the nails was wipe-resistant and waterproof. Special protection of the skin areas surrounding the nails and the application of plaster dressings were therefore not necessary. Because of the high water content of the preparations, the affected toenails were not additionally bathed.

After treatment for approximately 6 days, one of the patients removed the affected areas of the nail and the subungual tissue debris easily with a scraper. The severe nail brittleness had disappeared and the severe hyperkeratosis had improved to a medium degree of severity. After treatment for approximately 6 weeks, the second patient showed that his severe nail brittleness had disappeared and the severe hyperkeratosis was no longer present.

Both patients showed a good treatment result. The tolerability of the preparation according to the invention was very good. Both patients were very satisfied with the handleability in the application of the preparation.

We claim:

1. A method of hydrating brittle toenails or fingernails comprising applying to brittle toenails or fingernails a solution consisting of:
   urea in an amount from 15 percent by weight to 35 percent by weight based on the weight of the entire solution;
   a hydrophilic film-forming agent in an amount from 15 percent by weight to 35 percent by weight based on the weight of the entire solution, wherein the hydrophilic film-forming agent is a compound selected from acrylic/methacrylic acid ester copolymers, polyvinylpyrrolidones, polyvinyl alcohols, vinyl acetate/vinylpyrrolidone copolymers, vinyl acetate/crotonic acid copolymers, methyl vinyl ether/maleic acid copolymers, polyesters, polyester amides, carboxymethylcellulose, hydroxyethylcellulose, hydroxypropylcellulose, hydroxypropylmethylcellulose, and mixtures thereof; and
   an aqueous-alcoholic mixture that comprises an alcohol selected from methanol, ethanol, propanol, isopropanol, butanol, pentanol, hexanol, and mixtures thereof.

2. The method of claim 1, wherein the hydrophilic film-forming agent is a polyvinylpyrrolidone.

3. The method of claim 1, wherein the alcohol is ethanol, n-propanol, or isopropanol.

4. The method of claim 1, wherein the ratio of alcohol to water is from 9:1 to 1:9.

5. The method of claim 4, wherein the ratio of alcohol to water comprises 2 parts of alcohol to 3 parts of water.

6. The method of claim 1, wherein the amount of the aqueous-alcoholic mixture is from 30 percent by weight to 60 percent by weight, based on the weight of the entire solution.

7. The method of claim 1, wherein the amount of the aqueous-alcoholic mixture is from 35 percent by weight to 55 percent by weight, based on the weight of the entire solution.

8. The method of claim 1, wherein the amount of water is from 30 percent by weight to 60 percent by weight, based on the weight of the entire solution.

9. The method of claim 1, wherein the amount of water is from 35 percent by weight to 55 percent by weight, based on the weight of the entire solution.

10. The method of claim 1, wherein the hydrophilic film-forming agent is present in an amount from 17 percent by weight to 25 percent by weight, based on the weight of the entire solution.

11. The method of claim 1, wherein the aqueous solution comprises water in an amount from 30% by weight to 60% by weight, based on the weight on the entire solution.

* * * * *